US008810637B2

(12) United States Patent  
Chatenever et al.

(10) Patent No.: US 8,810,637 B2  
(45) Date of Patent: Aug. 19, 2014

(54) UNIVERSAL CAMERA CONTROL UNIT

(75) Inventors: David Chatenever, Santa Barbara, CA (US); Marc R. Amling, Santa Barbara, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 1467 days.

(21) Appl. No.: 11/695,960

(22) Filed: Apr. 3, 2007

(65) Prior Publication Data

US 2008/0246838 A1 Oct. 9, 2008

(51) Int. Cl.  
*A62B 1/04* (2006.01)

(52) U.S. Cl.  
USPC .......................................................... 348/65

(58) Field of Classification Search  
USPC ........................................ 348/45, 61, 65–77  
See application file for complete search history.

(56) References Cited

U.S. PATENT DOCUMENTS

| | | | | |
|---|---|---|---|---|
| 4,769,693 A * | 9/1988 | Kato | | 348/269 |
| 5,347,991 A * | 9/1994 | Nakao et al. | | 600/156 |
| 5,589,874 A * | 12/1996 | Buchin | | 348/72 |
| 5,740,801 A | 4/1998 | Branson | | |
| 5,877,819 A | 3/1999 | Branson | | |
| 6,471,649 B1 * | 10/2002 | Saccardo et al. | | 600/437 |
| 6,642,953 B1 * | 11/2003 | Nieto Velasco et al. | | 348/61 |
| 6,768,774 B1 * | 7/2004 | MacInnis et al. | | 375/240.15 |
| 6,895,052 B2 * | 5/2005 | Hanamura et al. | | 375/240.03 |
| 7,349,098 B2 * | 3/2008 | Li | | 356/479 |
| 7,751,185 B2 * | 7/2010 | Yu | | 361/679.41 |
| 7,855,727 B2 * | 12/2010 | Adler et al. | | 348/65 |
| 7,978,189 B2 * | 7/2011 | Sprague et al. | | 345/204 |
| 8,199,187 B2 * | 6/2012 | Knapp et al. | | 348/65 |
| 8,289,381 B2 * | 10/2012 | Bayer et al. | | 348/65 |
| 8,325,224 B2 * | 12/2012 | Fukumoto | | 348/61 |
| 2002/0067408 A1 * | 6/2002 | Adair et al. | | 348/76 |
| 2002/0085091 A1 | 7/2002 | Takeshige et al. | | |
| 2002/0120885 A1 * | 8/2002 | Choi et al. | | 714/38 |
| 2003/0123856 A1 | 7/2003 | Chatenever et al. | | |
| 2003/0147004 A1 * | 8/2003 | Wang et al. | | 348/372 |
| 2004/0095507 A1 * | 5/2004 | Bishop et al. | | 348/441 |
| 2005/0140778 A1 * | 6/2005 | Kim et al. | | 348/14.02 |
| 2005/0253950 A1 | 11/2005 | Miura | | |
| 2006/0050144 A1 | 3/2006 | Kennedy | | |
| 2006/0055793 A1 | 3/2006 | Adler et al. | | |
| 2006/0072007 A1 * | 4/2006 | Gilor | | 348/61 |

(Continued)

FOREIGN PATENT DOCUMENTS

| | | |
|---|---|---|
| EP | 1286298 A2 | 2/2003 |
| GB | 2425424 A | 10/2006 |

(Continued)

OTHER PUBLICATIONS

Partial European Search Report, Aug. 18, 2008, 5 Pages.

(Continued)

*Primary Examiner* — Alicia Baturay  
(74) *Attorney, Agent, or Firm* — St. Onge Steward Johnston & Reens LLC (57) ABSTRACT

An endoscopic video system that provides for multiple differing inputs from a plurality of different attached devices types including, for example, High-Definition and Standard-Definition signals, the camera control automatically sensing and configuring itself based upon the connected devices (e.g. camera and display). The system further provides for scaling of input and output signals depending as necessary.

15 Claims, 7 Drawing Sheets

(56) References Cited

U.S. PATENT DOCUMENTS

| | | | |
|---|---|---|---|
| 2007/0070184 A1* | 3/2007 | Kim et al. | 348/14.02 |
| 2007/0161292 A1* | 7/2007 | Igarashi | 439/620.05 |
| 2007/0177008 A1* | 8/2007 | Bayer et al. | 348/65 |
| 2007/0177009 A1* | 8/2007 | Bayer et al. | 348/65 |
| 2007/0273786 A1* | 11/2007 | Ahn et al. | 348/373 |
| 2009/0085897 A1* | 4/2009 | Hirakawa et al. | 345/204 |
| 2009/0195692 A1* | 8/2009 | Ono | 348/553 |
| 2009/0231419 A1* | 9/2009 | Bayer | 348/76 |
| 2011/0018986 A1* | 1/2011 | Sprague et al. | 348/61 |

FOREIGN PATENT DOCUMENTS

| | | | |
|---|---|---|---|
| JP | 61175868 A | 8/1986 |
| JP | 62213073 A | 9/1987 |
| JP | 3156691 A | 7/1991 |
| JP | 10269344 A | 10/1998 |
| JP | 2000215033 A | 8/2000 |
| JP | 2000251393 A | 9/2000 |
| JP | 2002510823 T | 4/2002 |
| JP | 2002199291 A | 7/2002 |
| JP | 2003058872 A | 2/2003 |
| JP | 2003234939 A | 8/2003 |
| JP | 2004006189 A | 1/2004 |
| JP | 2004312468 A | 11/2004 |
| JP | 2004344555 A | 12/2004 |
| JP | 2005326684 A | 11/2005 |
| WO | 9952060 A2 | 10/1999 |

OTHER PUBLICATIONS

Extended European Search Report & European Search Opinion; Application No. 08006213.6; Nov. 11, 2008; 13 pages.
European Search Report Application No. EP 13 17 5797 Completed: Oct. 18, 2013; Mailing Date: Oct. 30, 2013 6 pages.

* cited by examiner

NTSC

INPUT

ACTIVE INPUT DATA: 483 X 1512

TOTAL INPUT DATA: 525 X 4680

OUTPUT

ACTIVE OUTPUT DATA: 1036 X 1386

TOTAL OUTPUT DATA: 1125 X 2184

UNIVERSAL CAMERA CONTROL UNIT

FIELD OF THE INVENTION

The invention relates to a multi-function camera control unit, and more particularly, to a camera control unit that is capable of receiving inputs from multiple different types of cameras having diverse signal formats and may generate diverse output signals compatible with differing displays.

BACKGROUND OF THE INVENTION

A Camera Control Unit ("CCU") is generally used in conjunction with a camera to capture and process images. The camera may include charge couple devices ("CCD"), CMOS devices or any other type of image capture device. They are typically used in conjunction with an endoscope to generate image data of an area to be viewed during a procedure. The image data is transmitted to the CCU. The CCU then processes the image data into displayable image data to be sent to a display. The CCU may also send commands to the camera in order to operate and adjust camera settings.

Known CCUs typically control a single type of camera by receiving and processing image data generated by the camera. The CCU controls the camera by adjusting color balance, light, focal distance, resolution, zoom, focus, shading, and other typical optical characteristics.

Traditionally, CCUs have been compatible with a limited number of devices because the control unit hardware, through which commands were sent and image signals were received, was difficult to configure to communicate with the many different types of devices in the market. For example, different devices may have varying electronic requirements/connections in order to function properly. Devices may be either analog or digital. In addition, some types of cameras are designated to pick up certain colors such as red or green while others pick up blue. In addition, as changes and improvements are made to devices, a control unit's hardware, which was configured to be compatible with older devices, may become incompatible and may need to be upgraded as well.

Because a CCU was compatible with limited quantities of devices, older CCUs were typically discarded in favor of CCUs that were made concurrently with particular devices. In order to address compatibility problems, configurable CCUs were introduced to function with a number of differing camera types.

For example, U.S. Pat. No. 5,627,583 ("Nakamura et al.") relates to an electroendoscope system that is compatible with a plurality of different endoscope types. However, Nakamura et al. fails to teach, disclose or suggest a system that is compatible with fundamentally differing signal types, such as for instance, a standard definition and a high-definition signal format. In addition, Nakamura et al. fails to teach or suggest a system that is compatible or usable with numerous differing display types, such as for instance, standard definition and high-definition displays. Therefore, while Nakamura et al. does provide for some versatility with regard to the attached camera, e.g. can configure itself to control the attached camera and receive the generated image signal, the CCU taught in Nakamura et al. is still limited to being able to receive a single type of image signal input (e.g. an analog input) and a single image signal format output (See, Col. 3, ln. 60—Col. 4, ln. 4; Col. 4, lns. 58-67).

SUMMARY OF THE INVENTION

What is desired, therefore, is to provide a system and method that is capable of maintaining compatibility different devices that may have fundamentally different signal formats.

It is also desired to provide a system and method that can automatically detect the type of device attached and can then automatically configure itself to be compatible with and control the attached device.

It is further desired to provide a system and method that is compatible with many different types of displays.

It is still further desired to provide a system and method that can automatically detect the type of connected display and can then automatically configure itself to be compatible with and control the attached display.

It is yet further desired to provide a system and method that can receive information from a connected device and automatically detect whether the received information is most up-to-date information for the attached device and if not, provide upgraded information to the attached device.

It is still further desired to provide a system and method that can accept either a standard or a high definition input signal from an input device and provide either a standard or a high definition output signal for an attached output device.

These and other objects are achieved in one advantageous embodiment in which a video imaging system is provided including a CCU the can automatically sense and identify a connected device, such as a camera, the CCU configuring and/or programming itself based on the identified device. A camera is provided to receive reflected light from an area to be viewed and for generation of image data representative of the reflected light. There are many different types of cameras and a number of different signal formats for the image data including, for example, Standard Definition (SD) and High Definition (HD) signals. In order to configure itself, the CCU retrieves and/or receives a program or multiple programs stored on a storage device. The retrieved program(s) execute on the camera control unit for enabling the camera control unit to process the image data. The digital input signal from an attached camera can vary widely, for example they may include but not are limited to ranges from 200×200 pixel resolution to 1920×1080 pixel resolution.

It is contemplated that the storage device may be any type of storage medium accessible by the control unit. For instance, it may be an internal, external, or removable drive and may also include a remote location, such as an Internet location. The storage device may also be located within the camera and/or the CCU. It is further contemplated that multiple storage devices and/or locations may be used to provide the latest version of software and/or programs for the configurable control unit.

In addition, the CCU also senses and identifies a connected display and configures an output signal to be compatible with the identified display. The output signal may variously be compatible with, for example, NTSC or PAL formats and may be provided as an SD or an HD signal. In addition to providing a compatible video signal output to an attached display, the CCU configures output control signals to properly control the attached display.

The CCU may be provided as a field programmable gate array (e.g. a configurable hardware device) or may be provided as a microprocessor or a Digital Signal Processor (DSP) (e.g. a soft configurable device). In any event, the CCU detects and identifies the connected device, e.g. a particular camera and/or a particular display, storage or other device, and configures itself to be compatible with the connected devices both for function and control. To function properly with a camera, the CCU will configure itself so as to be able to receive image data from and to be able to send command signals to the camera to control, for example, the camera's optical functional characteristics including: focal distance, resolution, light balance or color and the like.

In one advantageous embodiment, the CCU is provided with a microprocessor that receives a processor program for programming the microprocessor and a device program for programming and/or configuring the configurable device to process the received image data.

The term "data" as used herein means any indicia, signals, marks, symbols, domains, symbol sets, representations, and any other physical form or forms representing information, whether permanent or temporary, whether visible, audible, acoustic, electric, magnetic, electromagnetic or otherwise manifested. The term "data" as used to represent predetermined information in one physical form shall be deemed to encompass any and all representations of the same predetermined information in a different physical form or forms.

The term "network" as used herein includes both networks and internetworks of all kinds, including the Internet, and is not limited to any particular network, inter-network, or intra-network.

The terms "coupled", "coupled to", and "coupled with" as used herein each mean a relationship between or among two or more devices, apparatus, files, programs, media, components, networks, systems, subsystems, and/or means, constituting any one or more of (a) a connection, whether direct or through one or more other devices, apparatui, files, programs, media, components, networks, systems, subsystems, or means, (b) a communications relationship, whether direct or through one or more other devices, apparatui, files, programs, media, components, networks, systems, subsystems, or means, and/or (c) a functional relationship in which the operation of any one or more devices, apparatui, files, programs, media, components, networks, systems, subsystems, or means depends, in whole or in part, on the operation of any one or more others thereof.

In one advantageous embodiment, a video endoscopic system is provided comprising, a camera for generating image data and a display for displaying the image data. The system further comprises a camera control unit coupling the camera to the display. The camera control unit has a first input for transmitting and receiving a first signal format and a second input for transmitting and receiving a second signal format that is different from the first signal format. The camera control unit also has an output for transmitting the image data to the display.

In another advantageous embodiment, a method for transmitting image data from multiple cameras having differing signal formats to a camera control unit and a display is provided comprising the step of providing, a first receptacle and a second receptacle in the camera control unit, the first receptacle having a first configuration and the second receptacle having a second configuration that is different from the first configuration. The method further comprises the steps of providing a camera having one of either a first plug configuration or a second plug configuration that couples to the first and second receptacle configurations respectively, coupling the camera to one of the first or second receptacles and receiving a camera identifier and a program. The method still further comprises the steps of configuring the camera control unit based on the camera identifier and received program, coupling the camera control unit to the display and receiving a display identifier. Finally, the method comprises the steps of configuring an output signal to be compatible with the connected display, transmitting image data to the display and displaying the image data on the display.

Other objects of the invention and its particular features and advantages will become more apparent from consideration of the following drawings and accompanying detailed description.

DETAILED DESCRIPTION OF THE INVENTION

Referring now to the drawings, wherein like reference numerals designate corresponding structure throughout the views.

Figure 1:
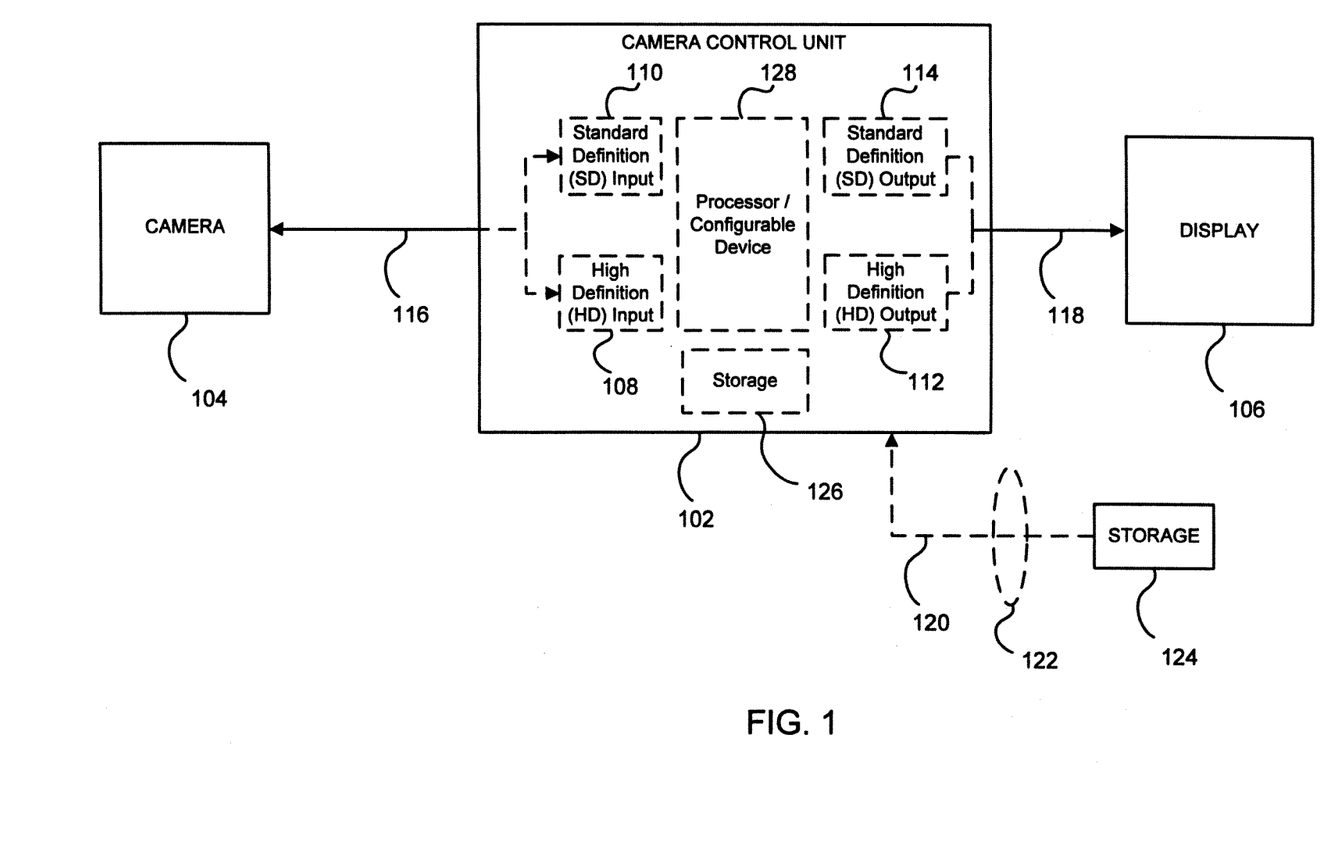
FIG. 1 is a block diagram of one advantageous embodiment of the present invention.

FIG. 1 depicts a system 100 comprising a camera 104 for generating image data. Camera 104 is connected to camera control unit 102 via a coupling 116. The coupling 116 is provided to supply electrical power to camera 104 as well as to transmit data between camera 104 and camera control unit 102. Camera control unit 102 is provided with at least two different inputs, including, a High-Definition (HD) Input 108 and a Standard-Definition (SD) Input 110. As used in this application, SD generally refers to a line count of up to approximately 720×480 NTSC and PAL; while HD refers to systems that utilize a higher line count and may include, for example but not limited to, 1280×720 progressive or 1920× 1080 or interlaced, which are only two of the commonly used HD resolutions. Depending on the camera type (SD or HD) a user will attach the camera to either the HD input 108 or the SD input 110.

Also shown in FIG. 1 is processor/configurable device 128 shown in camera control unit 102. Based on the connected camera, the camera control unit 102 will be configured to function with the connected camera 104 via either the HD input 108 or the SD input 110.

Two different output types are illustrated in FIG. 1 including, HD output 112 and SD output 114. It is contemplated that a display 106 may be connected to camera control unit 102 via a coupling 118. Upon connection, the camera control unit 102 can detect the attached display 106 and determine the correct signal format for proper functioning of display 106. For example, display 106 may be designed to display only SD video signals. That being the case, camera control unit 102 will transmit an SD signal format to display 106 whether an SD or an HD camera is connected. Alternatively, it may be determined that the connected display 106 may be designed to display HD video signals. In this case, if the connected camera 104 is an HD camera, an HD signal is transmitted to display 106. If however, an SD camera 104 is connected to camera control unit 102, an enhanced SD signal may be transmitted to the HD display 106. In this manner the following signal format types may be used $SD_{input} \rightarrow SD_{output}$; $SD_{input} \rightarrow$ Enhanced $SD_{output}$; $HD_{input} \rightarrow SD_{output}$; and $HD_{input} \rightarrow HD_{output}$. It should be noted that categorization of inputs and outputs as SD or HD is not intended to limit the categories to a single signal format, but rather, many differing signal formats may be categorized as SD and many differing signal formats may be categorized as HD.

It is contemplated that configuration information for either camera 104 and/or display 106 may be located on camera 104 and display 106 respectively. Alternatively, configuration information may be located in storage 126 that may comprise an internal storage device for camera control unit 102 with camera 104 and display 106 providing an identifier for camera control unit 102 to look up the correct configuration information. Still further, configuration information may be remotely located and may be transmitted to camera control unit 102 via a line 120 over a network connection 122 from a remote storage 124. The network connection 122 may include, for example, an Intranet, the Internet and/or the like.

Figure 2:
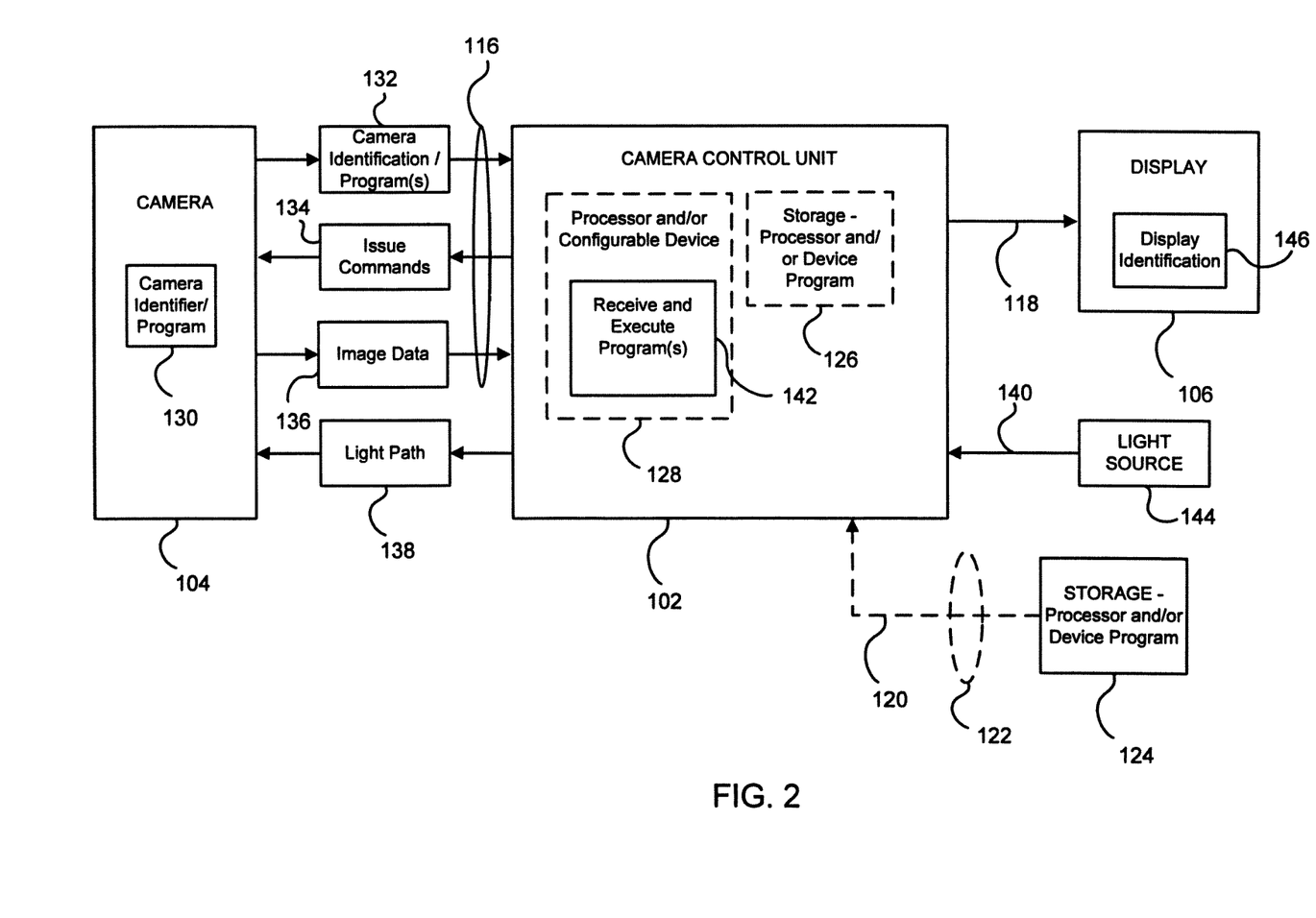
FIG. 2 is a block diagram of the advantageous embodiment according to FIG. 1.

Referring now to FIG. 2, an advantageous embodiment of the interaction between camera 104 and camera control unit 102 is illustrated. For example, upon connection of camera 104 to camera control unit 102, a camera identifier/program 130 stored on camera 104 may be transmitted as camera information/program(s) 132 to camera control unit 102. It is contemplated that the camera identifier may comprise discrete data or may comprise a program. In addition, it is contemplated that one or more programs may be stored on camera 104 and transmitted as or with the camera identification data. The processor and/or configurable device 128 receives the camera information/program(s) and executes the program(s) 142, which allows the processor and/or configurable device 128 to receive and process image data generated and transmitted by camera 104.

It is further contemplated that one or more programs may be located on internal storage 126 or may be located on remote storage 124. For example, upon connection of camera 104 to camera control unit 102, camera identifier 130 may be transmitted to camera control unit 102. Once identified, a program(s) may be transmitted to processor and/or configurable device 128 from camera 104, internal storage 126 or remote storage 124.

Once processor and/or configurable device 128 is properly configured to function with camera 104, camera control unit 102 may issue commands 134 to camera 104, for example, to adjust color balance, light, focal distance, resolution, zoom, focus, shading, and other optical characteristics. Camera 104 may then generate and transmit image data 136, which is received and processed by camera control unit 102. Image data received and processed by camera control unit 102 is then transmitted in the proper signal format to display 106.

Also illustrated in FIG. 2 is light path 138, 140 and light source 144. It is contemplated that light source 144 may comprise virtually any type of commonly used light source including, for example, a Light Emitting Diode while the light path may comprise, for instance, a coherent or non-coherent fiber optic bundle. While the light path 138, 140 is illustrated passing through camera control unit 102, it is contemplated that the light path may be separate and apart from camera control unit 102. Additionally, it is contemplated that light path 138 may be combined into coupling 116 or light source 144 may be provided in camera 104, or camera control unit 102.

Figure 3:
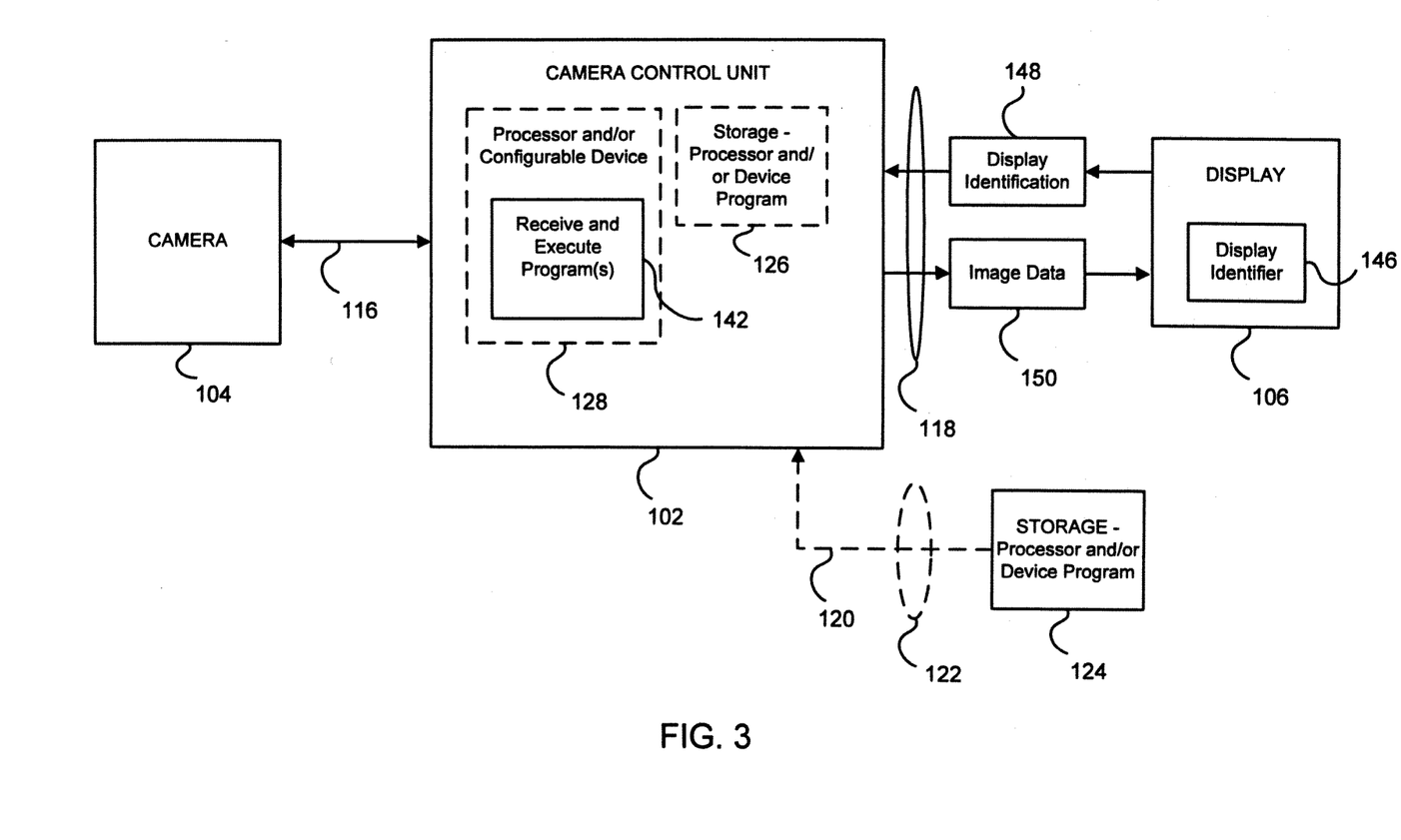
FIG. 3 is a block diagram of the advantageous embodiment according to FIG. 1.

FIG. 3 illustrates still another advantageous embodiment of the present invention. In this embodiment, display identifier 146 stored on display 106 is transmitted as display identification 148 to camera control unit 102. Once received, camera control unit 102 will determine a signal format that will be compatible with display 106. Image data 150 will then be transmitted to display 106 in the properly configured signal format.

There are commonly used types of signal formats that are typically used, however, it is contemplated that additional formats may be provided for and especially new signal formats that may become available. The two commonly used SD format types are NTSC and PAL. It should be noted that these are just two video signal formats and that there are many differing types and modifications to the above-listed types including, for example, a modified version Phase-Alternating Line (PAL-M). In any event, upon receipt of display information 148, camera control unit 102 can retrieve information and/or a program from, for example, internal storage 126, remote storage 124 or even from display 106 for configuration of the output signal for sending image data 150 in the proper format.

A number of examples will be provided of the input and output dimensions for HD resampling of NTSC and PAL formats. The following examples are presented to further illustrate and explain the present invention and should not be taken as limiting in any regard.

EXAMPLE 1

For NTSC the Specifications in One Advantageous Embodiment are as Follows

Figure 7:
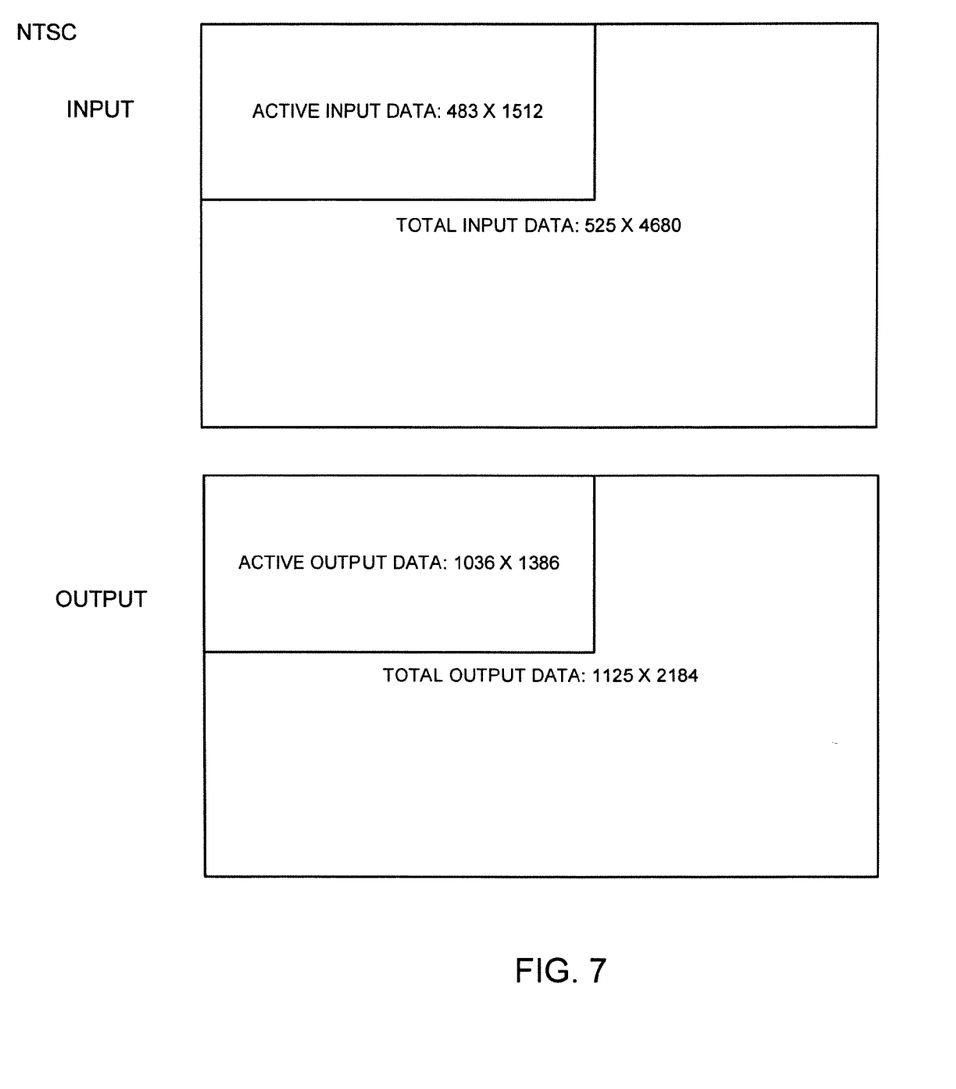
FIG. 7 is an illustration of input and output dimension for HD project resampling for NTSC.

Active data: 484×756
Pixel dimensions: 4.75 H×5.55 V
FPS: 60/1.001=59.9401
Data stream (input and output) is running at 147.2727 MHz.
Dimensions of Total Input Data (Active and Inactive).
Total number of input lines: 525. To find the total number of pixels per line: in 1 second there are $145.2727 \times 10^6$ pixels. Also, in 1 second there are 60/1.001 frames of (525×total number of pixels per input line $(145.2727 \times 10^6/((60/1.001) \times 525)=4680$.
Dimensions of Total Output Data (Active and Inactive).
Total number of output lines: 1125. We can use the fact that the input and output frame correspond to the same frame time. The total number of pixels per output line is then: (525× 4680)/1125=2184.
Dimensions of Active Input Data.
Out of a total of 525 lines, we assume that 483 contain valid data (active lines). The number of input active lines is: 483. The number of pixels per active line is: 756 oversampled by 2=1512. The active lines need to be resampled (vertically) by a factor of 1125/525. The number of output lines is: 483× 1125/525=1035. It should be noted that, in this case, 1125/525 gives an integer value so we can work with; 1125/525 or 1035/483. Otherwise, the active line ratio should be used. To determine the number of output pixels, we consider the ratio of vertical resampling as well as the fact that the pixels need to be converted to square dimension. The number of output square pixels=(1512/2×(4.75H/5.55V))×(1035/483) =1386.5~1386. FIG. 7 illustrates these numbers.

EXAMPLE 2

For PAL the Specifications in One Advantageous Embodiment are as Follows

Active data: 576×742
Pixel dimensions: 4.85 H×4.65 V
FPS: 50 (exactly)
Data stream (input and output) is running at 127.6875 MHz.
Dimensions of Total Input Data (Active and Inactive).
Total number of input lines: 625. To find the total number of pixels per line: in 1 second there are $127.6875 \times 10^6$ pixels.

Also, in 1 second there are 50 frames of (625×total number of pixels per input line (127.6875×10$^6$/(50×625)=4086.

Dimensions of Total Output Data (Active and Inactive).

Total number of output lines: 1125. We can use the fact that the input and output frame correspond to the same frame time. The total number of pixels per output line is then: (625×4086)/1125=2270.

Dimensions of Active Input Data.

Figure 8:
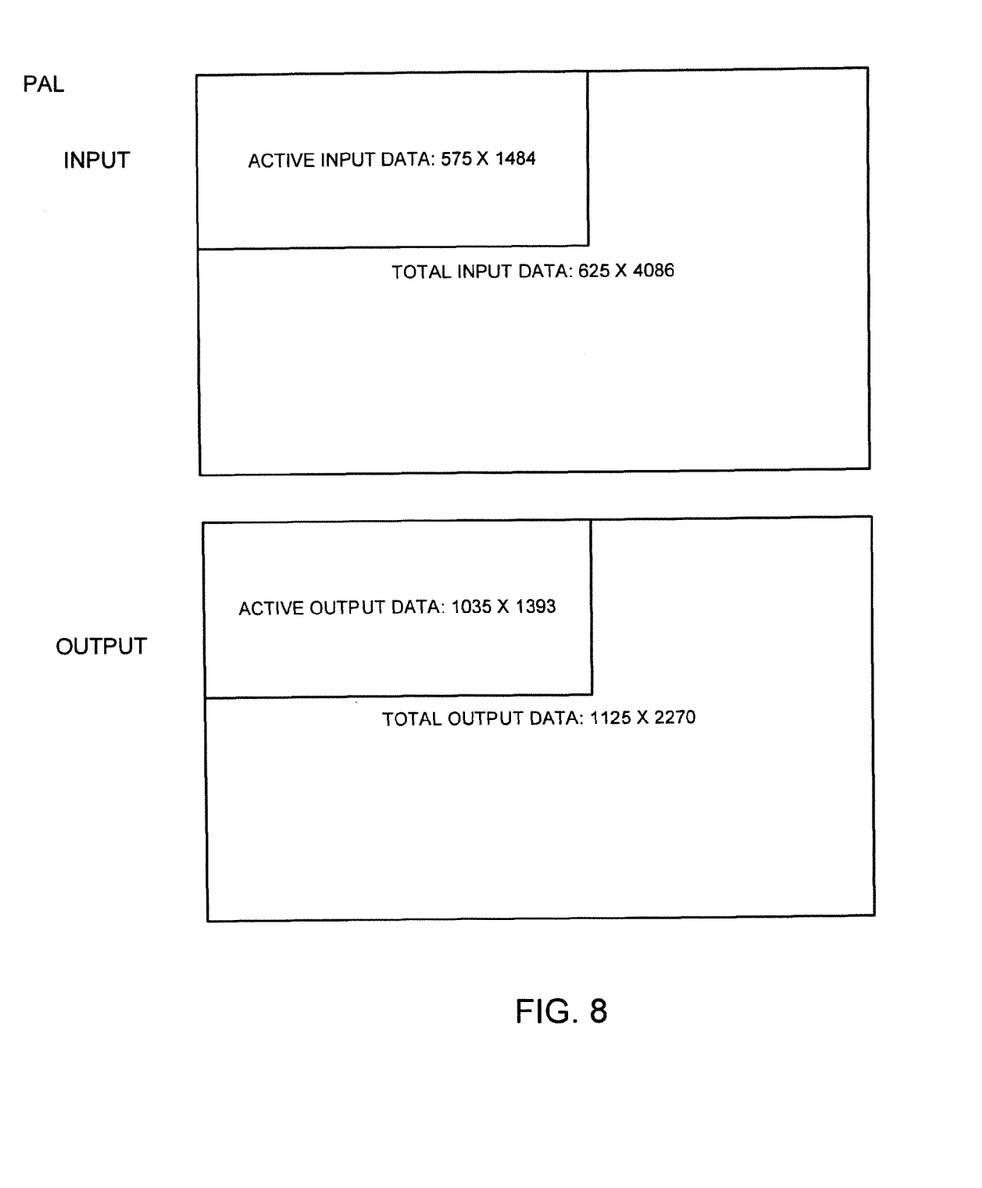
FIG. 8 is an illustration of input and output dimension for HD project resampling for PAL.

Out of a total of 625 lines, we assume that 573 contain valid data (active lines). The number of input active lines is: 575. The number of pixels per active line is: 742 oversampled by 2=1484. The active lines need to be resampled (vertically) by a factor of 1125/625. The number of output lines is: 575×1125/625=1035. To determine the number of output pixels, we consider the ratio of vertical resampling as well as the fact that the pixels need to be converted to square dimension. The number of output square pixels=(1484/2×(4.85H/4.65V))×(1035/575)=1393. FIG. 8 illustrates these numbers.

In addition to the standard NTSC and PAL SD (NTSC and PAL) composite, RGB, and s-video (Y/C) outputs, numerous other outputs may be used. The following examples are presented to further illustrate and explain the present invention and should not be taken as limiting in any regard.

Serial Digital Interface (SDI), standardized in ITU-R BT.656 and SMPTE 259M, is a digital video interface used for broadcast-grade video. A related standard, known as High Definition Serial Digital Interface (HD-SDI), is standardized in SMPTE 292M and provides a nominal data rate of 1.485 Gbit/s.

Digital Visual Interface (DVI) is a video interface standard designed to maximize the visual quality of digital display devices such as flat panel LCD computer displays and digital projectors and is partially compatible with the HDMI standard in digital mode (DVI-D). The DVI interface uses a digital protocol in which the desired illumination of pixels is transmitted as binary data. When the display is driven at its native resolution, it will read each number and apply that brightness to the appropriate pixel. In this way, each pixel in the output buffer of the source device corresponds directly to one pixel in the display device.

High-Definition Multimedia Interface (HDMI) is an all-digital audio/visual interface capable of transmitting uncompressed streams. HDMI is compatible with High-bandwidth Digital Content Protection (HDCP) Digital Rights Management technology. HDMI provides an interface between any compatible digital audio/video source and a compatible digital audio and/or video monitor, such as a digital television (DTV).

Figure 4:
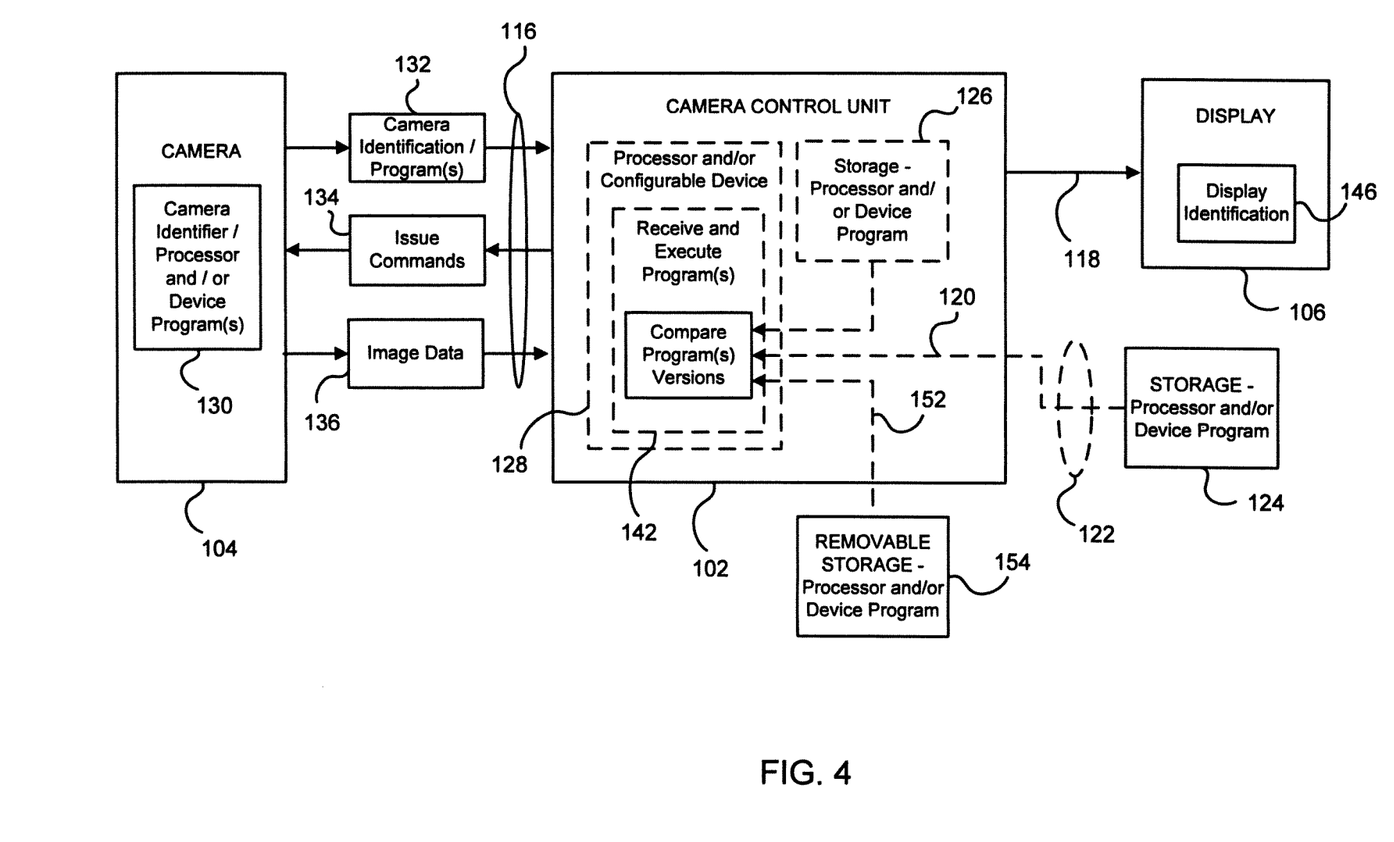
FIG. 4 is a block diagram of the advantageous embodiment according to FIG. 1.

Referring now to FIG. 4 it is contemplated that a storage device for storing the program(s) for configuration of the processor and/or configurable device 128 may reside on camera 104, internal storage 126, a removable storage 154 (e.g. a removable drive or storage medium) or a remote storage 124 (e.g. via a network connection). In this manner, when the camera control unit 102 receives the camera identification/program(s) 132 from camera 104, camera control unit 102 can compare program(s) versions from the various storage mediums to determine if the camera identification/program(s) received from camera 104 is the latest version and if not, the camera information can be updated. This can happen automatically, or the system could, for example, prompt the user to decide whether or not to update the camera information. In addition, it is contemplated that based upon user access, certain programs and/or features may become available.

Figure 5:
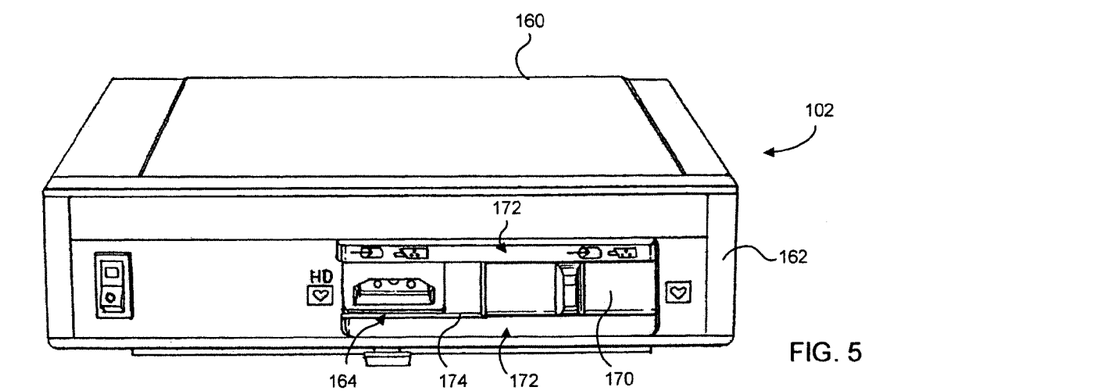
FIG. 5 is an illustration of the Camera Control Unit according to the advantageous embodiment of FIG. 1.
Figure 6:
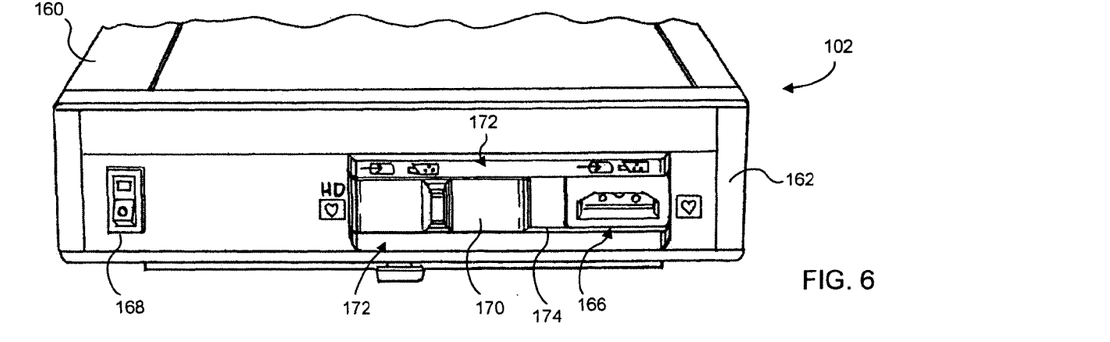
FIG. 6 is an illustration of the Camera Control Unit according to the advantageous embodiment of FIG. 1.

FIGS. 5 and 6 illustrate the camera control unit 102 per one embodiment of the present invention. Camera control unit 102 includes a case 160 having a front panel 162. Front panel 162 is provided with multiple inputs including, an HD receptacle 164 and an SD receptacle 166. In addition, a power switch 168 may also be positioned on front panel 162. Also positioned on front panel 162 is slideable door 170 and tracks 172. It is contemplated that a camera 104 is provided with a plug (not shown) that, based upon the camera configuration (e.g. either HD or SD), is keyed to fit in either HD receptacle 164 or SD receptacle 166. The door 170 may simply be slid to cover the receptacle that is not currently in use. The door is provided with a protrusion(s) (not shown) that engage with a channel 174 provided in tracks 172 so as to capture door 170 but still allow for lateral sliding action.

It should be noted that, while HD receptacle 164 and SD receptacle 166 are not illustrated including an optical connection or coupling, it is contemplated that they may be provided with such.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A video endoscopic system comprising:
 a camera for generating image data;
 a display for displaying the image data;
 a camera control unit coupling said camera to said display, said camera control unit having:
  a first receptacle for receiving image data having first signal format;
  a second receptacle for image data having second signal format that is different from said first signal format;
  an output for transmitting the image data to said display; and
 a door that alternatively covers one of either the first or the second receptacles, wherein said door is slideable such that when the door covers said first receptacle, said second receptacle is exposed and when said door covers said second receptacle, said first receptacle is exposed;
 at least two tracks engaging with said slideable door, each track having a recess, and said slideable door comprises at least two protrusions that engage with said recesses;
 wherein upon connection with said display, said camera control unit determines a compatible output signal for said display.

2. The video endoscopic system according to claim 1 wherein said first receptacle is configured to receive a first plug and said second receptacle is configured to receive a second plug, where said first and second plugs comprise different configurations.

3. The video endoscopic system according to claim 1 wherein said first input comprises High-Definition (HD) input image data, and said second input comprises a Standard-Definition (SD) input image data.

4. The video endoscopic system according to claim 1 wherein the output signal format is selected from the group consisting of: NTSC, PAL, Serial Digital Interface (SDI), High Definition Serial Digital Interface (HD-SDI), Digital Visual Interface (DVI), High-Definition Multimedia Interface (HDMI) and combinations thereof.

5. The video endoscopic system according to claim 1 wherein upon connection of said camera to said camera control unit, camera information is transmitted to said camera control unit and said camera control unit is configured to be compatible with said camera.

6. The video endoscopic system according to claim 5 wherein said camera control unit further comprises a processor and a configurable portion.

7. The video endoscopic system according to claim 6 wherein processor information is used to program said processor and a device information is used to program the configurable portion.

8. The video endoscopic system according to claim 6 wherein said configurable portion is selected from the group consisting of: a field programmable gate array, a microprocessor, a digital signal processor and combinations thereof.

9. The video endoscopic system according to claim 1 wherein said camera is coupled to an endoscope via a coupling mechanism.

10. The video endoscopic system according to claim 9 further comprising an illumination channel coupled to the endoscope, said illumination channel directing illuminating light to the endoscope from a light source.

11. A method for transmitting image data from multiple cameras having differing signal formats to a camera control unit and a display via a camera control comprising the steps of:

providing a first receptacle and a second receptacle in the camera control unit, the first receptacle having a first configuration and the second receptacle having a second configuration that is different from the first configuration;

providing a door that alternatively covers one of either the first or the second receptacles, wherein said door is slideable such that when the door covers said first receptacle, said second receptacle is exposed and when said door covers said second receptacle, said first receptacle is exposed;

providing at least two tracks engaging with said slideable door, each track having a recess, and said slideable door comprises at least two protrusions that engage with said recesses;

providing a camera having one of either the first plug configuration or the second plug configuration that couples to the first or second receptacle configurations respectively;

coupling the camera to one of the first or second receptacles;

receiving camera information;

configuring the camera control unit based on the camera information;

coupling the camera control unit to the display and identifying the display;

the camera control unit configuring an output signal to be compatible with the connected display;

transmitting the image data to the display; and displaying the image data on the display.

12. The method according to claim 11 further comprising the step of selectively covering one of the first or second receptacles with a slideable door.

13. The method according to claim 11 wherein said first input is a High-Definition (HD) image data input, and said second input is a Standard-Definition (SD) image data input.

14. The method according to claim 13 further comprising the steps of scaling the image data received from the camera to a scaled size formally compatible with the identified display.

15. The method according to claim 14 wherein when the identified display is compatible with NTSC the HD image data is scaled according to a first process, and when the display is compatible with PAL the SD image data is scaled according to a second process that is different from the first process.

* * * * *